(12) United States Patent
Moosmuller et al.

(10) Patent No.: US 6,542,831 B1
(45) Date of Patent: Apr. 1, 2003

(54) VEHICLE PARTICULATE SENSOR SYSTEM

(75) Inventors: Hans Moosmuller, Reno, NV (US); Robert E. Kcislar, Reno, NV (US)

(73) Assignee: Desert Research Institute, Reno, NV (US)

( * ) Notice: Subject to any disclaimer, the term of this patent is extended or adjusted under 35 U.S.C. 154(b) by 0 days.

(21) Appl. No.: 09/838,474

(22) Filed: Apr. 18, 2001

Related U.S. Application Data

(60) Provisional application No. 60/198,495, filed on Apr. 18, 2001.

(51) Int. Cl.[7] ................................. G06F 7/06
(52) U.S. Cl. ........................... 702/40; 702/24; 702/26; 702/29; 702/30
(58) Field of Search .......................... 702/40, 134, 172, 702/24, 26, 27, 29, 30; 340/901, 902, 904, 905

(56) References Cited

U.S. PATENT DOCUMENTS

| | | | |
|---|---|---|---|
| 3,609,378 A | 9/1971 | Smith, Jr. ............... | 250/217 |
| 5,210,702 A | 5/1993 | Bishop et al. ............ | 364/496 |
| 5,418,366 A | 5/1995 | Rubin et al. ............ | 250/338.5 |
| 5,574,286 A | 11/1996 | Huston et al. ........... | 250/372 |
| 5,663,710 A * | 9/1997 | Fasig et al. ............. | 340/601 |
| 5,726,450 A | 3/1998 | Peterson et al. ......... | 250/338.5 |
| 5,767,519 A | 6/1998 | Grelbwachs ............. | 250/372 |
| 5,818,583 A | 10/1998 | Sevick-Muraca et al. ... | 356/336 |
| 5,877,862 A | 3/1999 | Nelson et al. ........... | 356/436 |
| 5,914,776 A * | 6/1999 | Streicher ................ | 356/5.01 |
| 6,069,565 A * | 5/2000 | Stern et al. ............. | 340/583 |

* cited by examiner

Primary Examiner—Marc S. Hoff
Assistant Examiner—Felix Suarez
(74) Attorney, Agent, or Firm—Ian F. Burns

(57) ABSTRACT

An apparatus for measuring particles in an exhaust gas of a vehicle. A transmitter is adapted to provide a source of ultraviolet radiation. The radiation travels through the gas and impinges upon the particles in the gas generating a backscattered radiation. The transmitter also generates a timing signal. A receiver is located in proximity of the transmitter. The receiver is adapted to receive the backscattered radiation and to generate a backscattered signal indicative of the quantity of particles entrained in the gas. A data system is connected to the receiver, the data system is adapted to receive the timing signal and the backscattered signal as an input and to calculate a quantity of particles in the gas at a location from the transmitter.

30 Claims, 6 Drawing Sheets

VEHICLE PARTICULATE SENSOR SYSTEM

CROSS REFERENCES TO RELATED APPLICATIONS

This application claims priority to U.S. provisional patent application serial No. 60/198,495, filed Apr. 18, 2001.

BACKGROUND OF THE INVENTION

1. Field of Invention

This invention relates to a remote sensing device that is used to detect and measure particulate matter emissions from vehicles.

2. Description of Related Art

Remote sensing of vehicle exhaust has been shown to be an economical method to determine on-road emissions for thousands of vehicles per day.

A Remote Sensing Device (RSD) is placed on the side of a one-lane road, often a freeway onramp. It measures the gaseous emissions of individual passing vehicles. The main gases of interest are carbon monoxide (CO), hydrocarbons (HC), nitrous oxides ($NO_x$), and carbon dioxide ($CO_2$) as exhaust plume dilution tracer. For example, the Fuel Efficiency Automobile Test (FEAT) system uses absorption measurements in the infrared and ultraviolet spectral regions to determine column concentrations of CO, $CO_2$, HC, and NO in the exhaust plume of each passing vehicle. By determining the ratio of CO, HC, and NO to $CO_2$, emission factors (per unit fuel consumption) can be derived. Remote sensing devices may also employ ancillary devices to register speed, acceleration, and the license plate for each passing vehicle. These data help with the further interpretation and use of the measurements of gaseous emissions. The practical and commercial applications of the remote sensing devices for gaseous emissions are currently mainly in three areas:

1. Gross Emitter Identification: Vehicles with emissions of gaseous pollutants exceeding emission standards are identified. Vehicle owners are notified and required to bring the vehicle into compliance with emission standards.
2. Clean Screening: Vehicles with emissions of gaseous pollutants in compliance with emission standards are identified. Vehicle owners are notified that they have passed the smog check and can reregister their vehicle after paying the usual inspection and maintenance fee. Part of this fee funds the remote sensing program.
3. Evaluation of Fleet Emissions: The statistical distribution of emission rates over different vehicle fleets is evaluated with remote sensing. This information is valuable from a scientific point of view and important for areas in non-attainment with air quality standards to devise a plan (e.g., state implementation plan) to come into compliance in a cost-effective manner.

In addition to gaseous pollutants, there is interest in developing remote sensing methods for measuring on-road particulate matter emissions from vehicles. Measurements of particulate matter mass emissions from the tail-pipes of vehicles can be made on a dynamometer with direct collection onto filters. However, this method is orders of magnitudes more expensive than on-road remote sensing measurements and only small numbers of vehicles have been tested. This is due to the need of pulling vehicles over and testing them individually on a (portable) dynamometer. Therefore, only a small fraction of the vehicles passing by can be tested.

On-road measurements of light absorbing particle emissions have been made both with an aethalometer and with the University of Denver (DU) opacity method. Both methods, as implemented, are only sensitive to the black carbon (BC) mass component of particulate mass emissions. For gasoline combustion engines, particulate mass emissions are generally dominated by organic carbon (OC) mass, while for diesel engines either BC or OC can be the dominant component. In addition, aethalometer measurements cannot assign emissions to single vehicles in dense traffic, and the DU method is relatively insensitive and cannot distinguish between road-dust opacity and exhaust opacity. Road dust opacity can be a significant part of the total opacity, especially if the remote sensor makes measurements near the road surface level as commonly done for vehicles with tailpipes mounted below the main vehicle body. The in-situ aethalometer technique relies on collecting a plume sample and therefore must be located down-wind of the traffic flow, so that the exhaust plume is transported to the instrument inlets. This makes site selection much more difficult and often reduces the probability of a successful measurement.

The University of Denver (DU) opacity method uses the reference channel of a conventional RSD to measure infrared light extinction due to particles. This method yields only extinction values integrated across the road and is therefore not capable of distinguishing between tail pipe particle emissions and entrained road dust. As currently implemented (i.e., using infrared light), this method is also only sensitive to the black carbon (BC) mass component of particulate mass emissions. For gasoline combustion engines, particulate mass emissions are generally dominated by organic carbon (OC) mass, while for diesel engines either BC or OC can be the dominant component. In addition, the DU method is relatively insensitive as it measures an often small departure from the background signal of the reference beam.

What has long been needed is a sensor to measure particulate mass in a remote sensing device that can distinguish between road-dust particles and exhaust particles. Another long felt need is for a particulate sensor that also measures both black carbon particles and organic carbon particles. Another long felt need is for a particulate sensor that can measure particulate levels from multiple vehicles in dense traffic.

SUMMARY OF INVENTION

1. Advantages of the Invention

An advantage of the present invention is that it provides a particle measurement system for particles emitted in the exhaust gas of a vehicle.

Another advantage of the present invention is that it provides a vehicle particulate sensor that can discriminate between road dust and particles emitted by the vehicle.

A further advantage of the present invention is that it provides a vehicle particulate sensor that can quickly and easily be deployed by at a roadside location.

An additional advantage of the present invention is that it provides a vehicle particulate sensor that can measure the particulate emissions from multiple vehicles as they pass a test site.

Yet another advantage of the present invention is that provides a measurement of particulate emissions that can be combined for each vehicle with a measurement of carbon dioxide emissions. Thereby, a ratio of particulate emissions per volume of fuel can be calculated.

An advantage of the present invention is that it provides a vehicle particulate sensor that can detect both organic carbon and black carbon particles.

An additional advantage of the present invention is that it provides a vehicle particulate sensor that is insensitive to effects from visible light.

These and other advantages of the present invention may be realized by reference to the remaining portions of the specification, claims, and abstract.

2. Brief Description of the Invention

The present invention comprises an apparatus for measuring particles in a gas. A transmitter is adapted to provide a source of ultraviolet radiation. The radiation travels through the gas and impinges upon the particles in the gas generating a backscattered radiation. The transmitter also generates a timing signal. A receiver is located in proximity of the transmitter. The receiver is adapted to receive the backscattered radiation and to generate a backscattered signal indicative of the quantity of particles entrained in the gas. A data system is connected to the receiver, the data system is adapted to receive the timing signal and the backscattered signal as an input and to calculate a quantity of particles in the gas at a location from the transmitter.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF THE PREFERRED EMBODIMENT

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Particulate Sensor System

Figure 1:
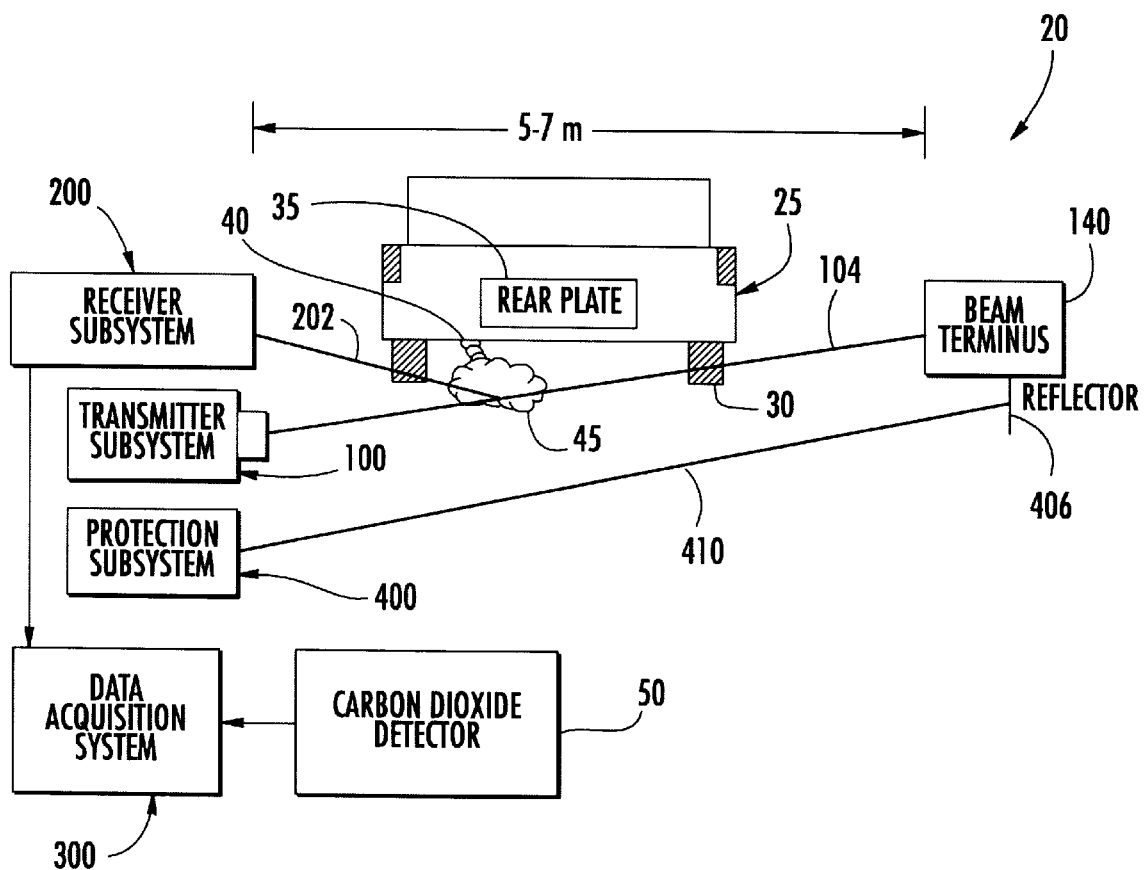
FIG. 1 is substantially a schematic view of the preferred embodiment of a vehicle particulate sensor system.

Referring now to FIG. 1, the present invention comprises a vehicle particulate sensor system 20 that is adapted to measure particles emitted in the exhaust gas of a vehicle 25. The vehicle is shown in rear view has spaced apart tires 30, a license plate 35, an exhaust pipe 40 and exhaust 45. Vehicle particulate sensor system 20 comprises a carbon dioxide detector 50, a transmitter 100, laser beam 104, beam terminus 140, receiver 200 and data system 300. Carbon dioxide detector 50 measures a level of carbon dioxide. Transmitter 100 emits a source of radiation such as a laser beam 104 across a road or vehicle path. The laser beam travels to beam terminus 140 where the laser beam is terminated. When the laser impinges upon particles entrained in the air, a backscattered light 202 is generated. The backscattered light is received by receiver 200. Receiver 200 generates a backscattered electrical signal that is proportional to the size and quantity of particles in the air between the transmitter and the beam terminus. A data system 300 receives the backscattered electrical signal and is able to calculate several particle parameters such as average particle density and particle densities at several distances from the transmitter. The carbon dioxide detector 50 is commercially available from various vendors (e.g., Environmental System products, Inc., Tucson, Ariz.).

Figure 2:
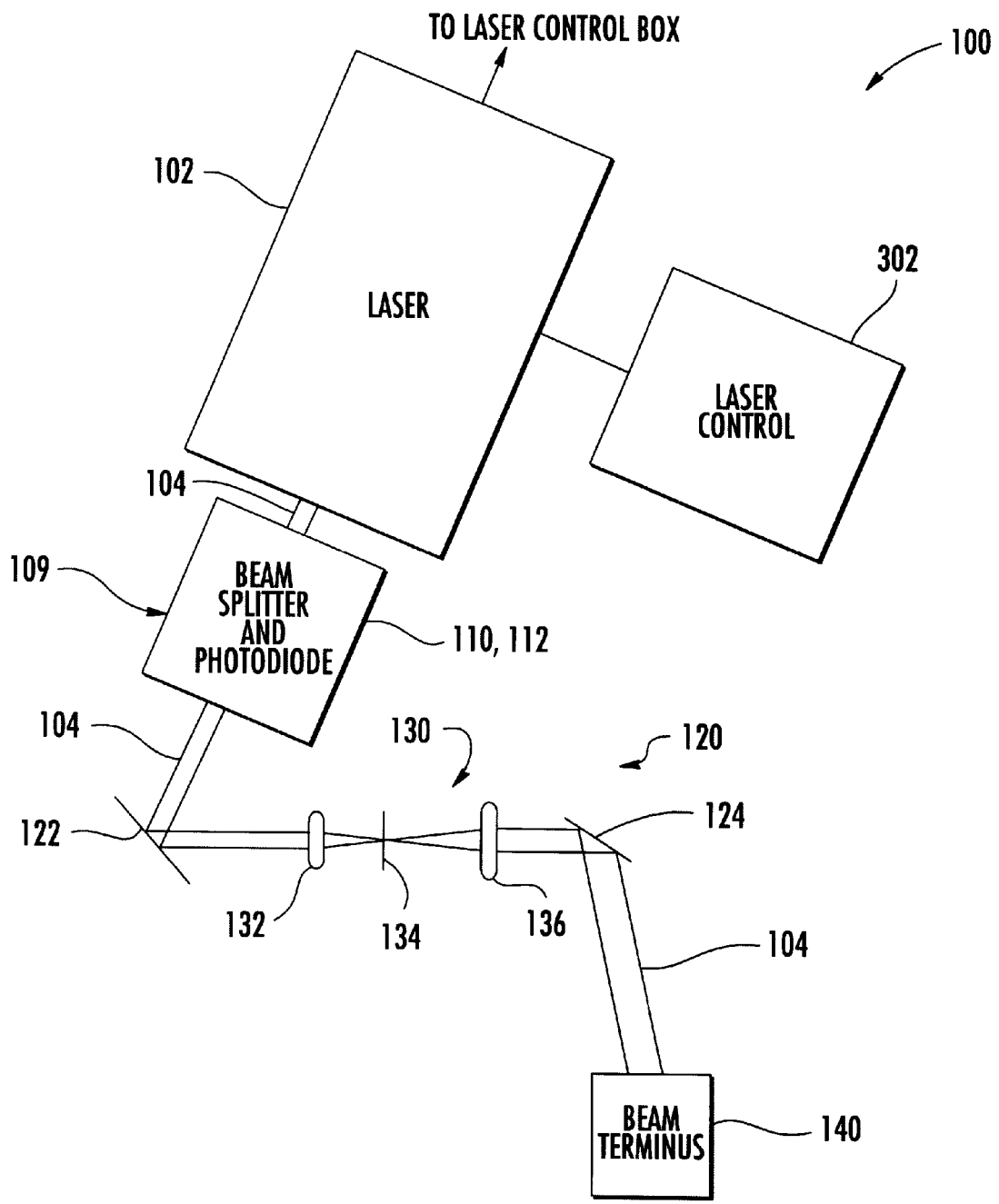
FIG. 2 is substantially a schematic view showing details of the transmitter of FIG. 1.

Turning now to FIG. 2, details of transmitter 100 are shown. Transmitter 100 comprises a pulsed UV laser 102, laser control 302, beam splitter 110, photodiode 112, beam-steering optics 120 and beam terminus 140. Laser 102 is a pulsed UV laser that is a passively Q-switched, diode-laser-pumped Nd:YAG laser with a primary operating wavelength of 1064 nm (near infrared). Integrated into the laser head is a frequency quadrupling system resulting in an output wavelength of 266 nm (solar blind ultraviolet). The laser emits light pulses of sub-nanosecond duration at a pulse repetition rate of about 6 kHz. Its average power is about 1 mW. This laser is a compact, robust, all-solid-state light source. It is commercially available from NanoLase through its US distributor Uniphase. Laser 102 emits a well-defined laser beam aligned relative to the field of view of the receiver. The laser 102 is controlled by a laser control 302. A timing or trigger signal generation unit 109 uses a beam-splitter 110 to split off a minor fraction of the laser beam and to direct it onto a fast photodiode 112. The electrical signal obtained from the photodiode when it is hit by a laser pulse serves as a timing signal for the data acquisition system. A complete parts list is shown in table 1.

A beam-steering optic assembly 120 comprises a first mirror 122 and a second mirror 124 mounted in adjustable mirror mounts capable of changing the laser beam direction upon reflection. Mirrors 122 and 124 are coated with UV-reflecting coatings such as Uv-enhanced aluminum coating. The beam steering optic assembly 120 directs the laser beam through a spatial filter 130 and aligns it relative to the field of view of the receiver 200. Spatial filter 130 improves the spatial mode quality of the laser beam to a near Gaussian distribution. The laser beam is fairly well defined, however it contains a small part of its energy in side modes, which diverge slowly from the main beam. These side modes would miss the entrance of the beam terminus 140 and generate an excessive backscatter signal. The same problem would also occur during system calibration. Therefore, these side modes are eliminated using spatial filter 130. The spatial filter comprises a focusing lens 132, a small aperture 134 (i.e., pinhole) to filter out the higher spatial frequencies and a collimating lens 136 to recollimate the laser beam. The spatial filter is commercially available from ThorLabs. The lenses 132 and 136 are fused silica lenses commercially available from optics suppliers such as Newport Corp. All transmission optics (i.e., lenses, windows, beamsplitters, etc.) are transparent at the ultraviolet (UV) laser wavelength of 266 nm and are made of UV-transmitting material such as fused silica.

A beam terminus 140 terminates the laser beam 104 on the other side of the road from the transmitter. The beam terminus provides a degree of safety by preventing the beam from continuing on toward people or objects. The beam terminus 140 also generates a well-defined reflection signal, which can be used to measure the opacity through the particle containing air. This measurement is also called a transmission measurement or an optical extinction measurement over the beam path. To reduce the dynamic range requirements on the receiver and data acquisition system, this reflection should be on the same order of magnitude as the scattering from vehicle-exhaust and/or entrained road dust, i.e., it has to be quite small. Therefore, the beam terminus has to be designed to reduce near-backscatter sufficiently. A beam terminus can be based on single or multiple reflections by light absorbing glass. Such a beam terminus, named the "Black Hole", is commercially manufactured by Blue Sky Research and distributed by ThorLabs. For the transmission or extinction measurement care has to be taken that the beam terminus is large enough to ensure uniform termination of both the laser beam and light near forward scattered by particles in the exhaust plume. Alternatively, the laser beam extinction can more directly be measured by a separate detector (e.g., UV photodiode) either placed on the opposite side of the road from the main instrument, or, through use of a mirror on the opposite road side, the detector can be placed on the same side of the road as the main instrument.

Figure 3:
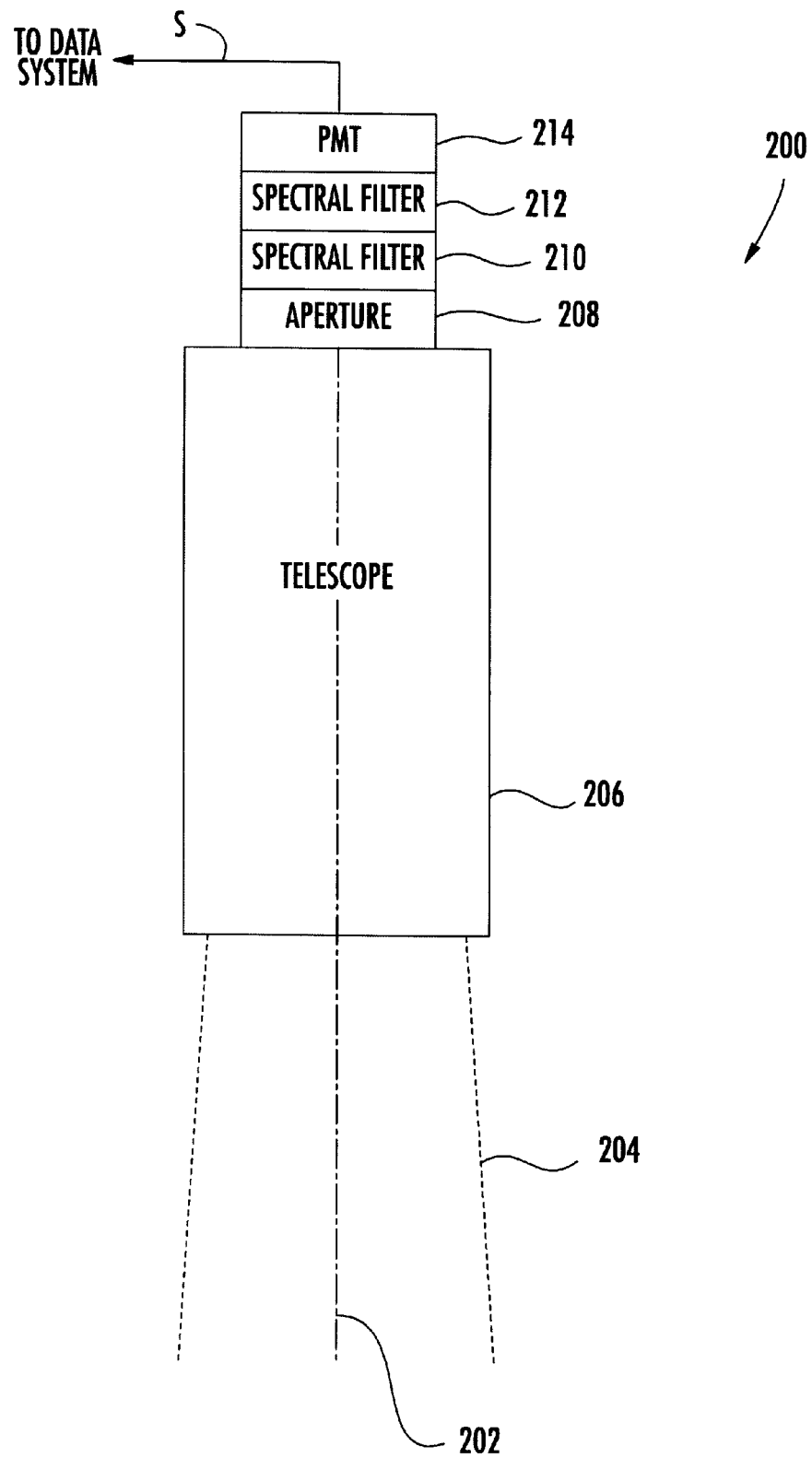
FIG. 3 is substantially a schematic view showing details of the receiver of FIG. 1.

Referring to FIG. 3, details of receiver 200 are shown. Receiver 200 collects backscattered laser light 202 that is backscattered after impinging upon the particles in the air, eliminates background light, and converts the backscattered laser light into an electronic signal. Receiver 200 comprises a telescope 206, an adjustable aperture 208, spectral filters 210 and 212 to block background light, and a photomultiplier tube 214 to generate an electrical backscatter signal from the backscattered light. The telescope 206, an adjustable aperture 208, spectral filters 210 and 212 to block background light, and a photomultiplier tube 214 are all attached adjacent each other. Telescope 206 uses a 2" diameter fused silica lens to collect backscattered light and to focus it through aperture 208. The telescope tubing and lens are available from ThorLabs. Adjustable aperture 208 is an iris diaphragm commercially available from ThorLabs. The aperture is located approximately in the image plane of the telescope. Changing the diameter of aperture 208 adjusts the telescope's field of view 204. Adjusting the field of view also changes the amount of overlap of individual distances or ranges that are sampled across the road.

Spectral filter 210 is a solar blind edge filter that blocks near-UV, visible, and infrared light. Spectral filter 212 is a bandpass filter that only transmits light very near the laser wavelength. Filters 210 and 212 are used together to increase the background light suppression relative to that obtained from just one filter. Spectral filters 210 and 212 are commercially available from Corion corporation.

The photomultiplier tube 214 (PMT) is a sensitive high-speed detector that converts the backscattered light 202 collected by the telescope into an electrical backscatter signal. photomultiplier tube 214 can be a photomultiplier tube with an integrated high voltage supply such as a Hamamatsu H6780-06 with a rise-time of 0.78 ns. The backscatter signal is provided to the data system 300 for processing. The backscatter signal is about proportional to the number and size of the particles in the path of the laser beam if the total beam extinction (i.e., optical density) is low.

Figure 4:
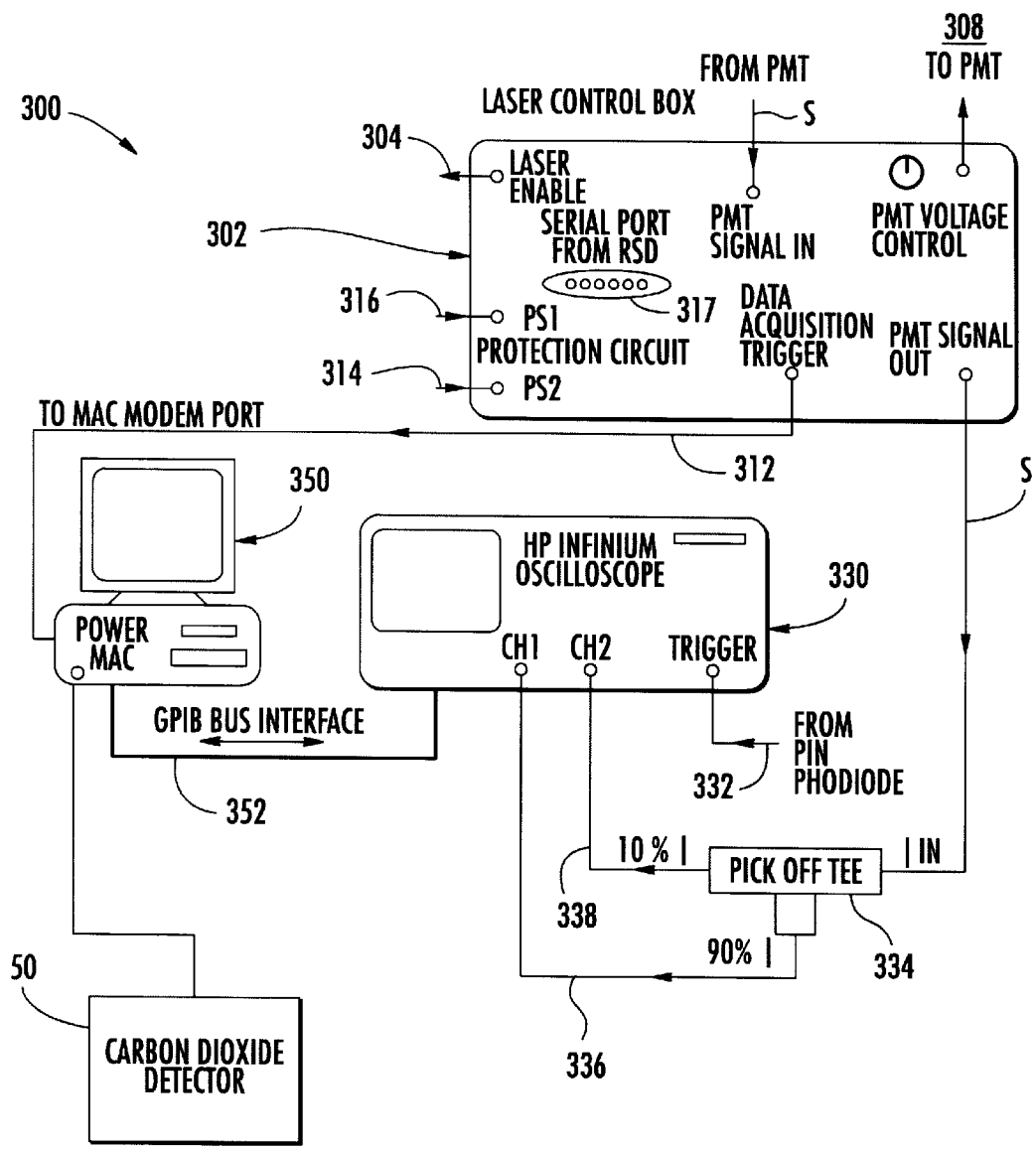
FIG. 4 is substantially a schematic view showing details of the data system of FIG. 1.

Turning now to FIG. 4, data system 300 is shown. Data system 300 receives the backscattered signal S from the PMT 214, digitizes it and analyzes it via a processor or computer. The data system 300 comprises a laser control 302, an analog-to-digital (A/D) converter 330, a general purpose interface bus 352 (GPIB) interface between the A/D converter and computer, and a computer or processor 350 for data acquisition and system control.

Laser control 302 generates a laser enable signal 304 to turn the laser 102 on and off. Laser control receives the backscattered signal S(r) from the photomultiplier tube. The laser control supplies a voltage 308 to the photomultiplier tube. The backscattered signal S(r) is outputted to a pick off tee 334. A data acquisition signal 312 is provided to the computer 350. Protection circuit signals 316 and 314 are provided to the laser control 302. A serial port 317 receives data from a remote sensing device (RSD).

The pick off tee 334 takes the backscattered signal S(r) and splits the signal into two parts 10% of the signal is sent as signal 338 to channel 2 of A/D converter 330. 90% of the signal is sent as signal 336 to channel 1. The purpose of the pick off tee is to increase the dynamic range of the instrument by providing nearly full signal to Channel 1 for better sensitivity in measuring low backscattering plumes and by providing a reduced input signal on Channel 2 for relatively high backscatter plumes. A carbon dioxide detector 50 provides a carbon dioxide signal 340 to a data acquisition card in the computer 350. The photodiode 112 provides a signal 332 to the A/D converter.

Analog-to-digital (A/D) converter 330 converts the backscattered signal from the PMT to a digital signal suitable for computer processing. The A/D converter 330 needs to have a large analog bandwidth and a high, single-shot sampling rate to achieve sufficient spatial resolution to function. Commercially available A/D cards for use in a personal computer (PC) have been available only up to 500 MHz bandwidth, which is not sufficient for the present application. The preferred A/D converter can be a 1.5 GHz, 8 Gs/s digital oscilloscope commercially available from Agilent Technologies. The oscilloscope is also used to display the timing and backscattered signals and to do initial signal averaging over multiple (typical between 16 and 128 ) laser pulses. The digital oscilloscope is connected to the computer 350 with a IEEE-488 interface bus 352. The bus 352 serves to transfer data to the computer and to control oscilloscope settings by the computer. Carbon dioxide detector 50 is connected to a data acquisition card in the computer 350. Data acquisition by the oscilloscope is triggered by the timing signal from the transmitter photodiode 112. The backscattered electrical signal can be simultaneously digitized onto channels with different sensitivity, to increase the dynamic range of the data acquisition. For this, the sensitivity of one channel is set to observe the background scattering signal from ambient air and the relatively weak signal from "clean" cars, while the second channel is operated with lower sensitivity to observe the larger signal from "dirty" cars.

Computer 350 can be an Apple power Macintosh computer. Computer 350 serves for data acquisition, storage, analysis, and display and also for system control. Computer 350 has an IEEE-488 interface card. The software used to operate these functions is written in LabView (National Instruments) a graphical programming language for data acquisition and analysis. LabView software provides for a convenient high level programming environment. The Labview software can also introduce some speed limitations into the system.

Figure 5:
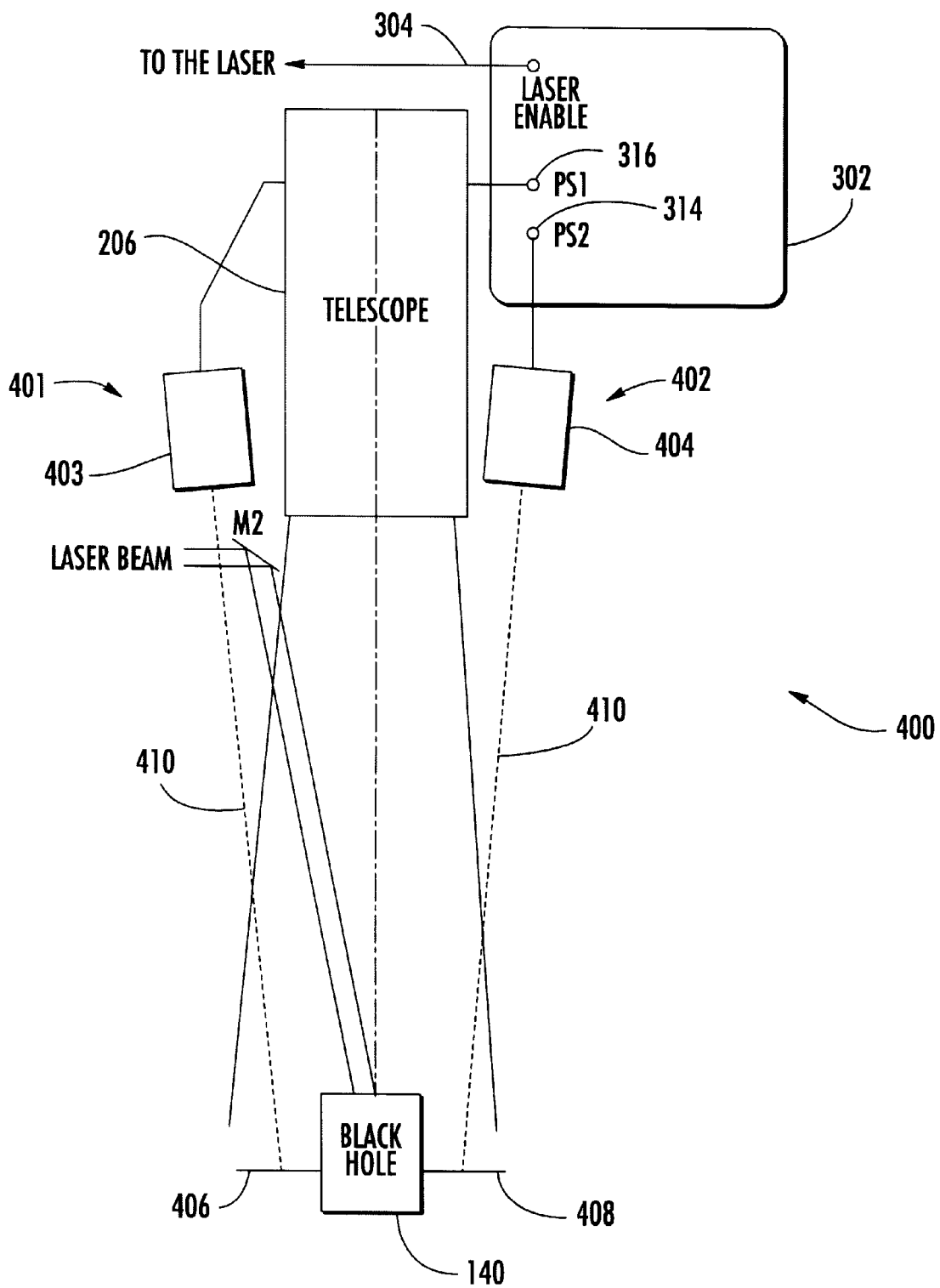
FIG. 5 is substantially a schematic view showing a protection mechanism used with the sensor of FIG. 1.

Referring to FIG. 5, a protection system 400 is shown mounted to telescope 206. protection system 400 comprises a pair of optical gates 401 and 402 mounted on each side of the laser beam adjacent the telescope. Each gate comprises a light source/detector assembly 403, 404 and a cat-eye type retro-reflector 406, 408. The reflector is mounted on each side of the beam terminus. The light source generates a light that travels on optical path 410. The detectors 403, 404 are electrically connected to the laser control 302 and supply the laser control 302 with a protection signals 314 and 316. If either of gates 401 or 402 are opened (i.e., the optical path blocked), laser control 302 switches the laser off. The protection system 400 functions as an eye safety feature if somebody should stick his/her head into the laser beam path, and to protect the PMT from excessive signal levels. Such excessive signal levels can, for example, be generated while a car passes through the sensor. The optical gates 401 and 402 are commercially available from Honeywell Corporation and are similar to those used to shut off motorized garage door openers.

Figure 6:
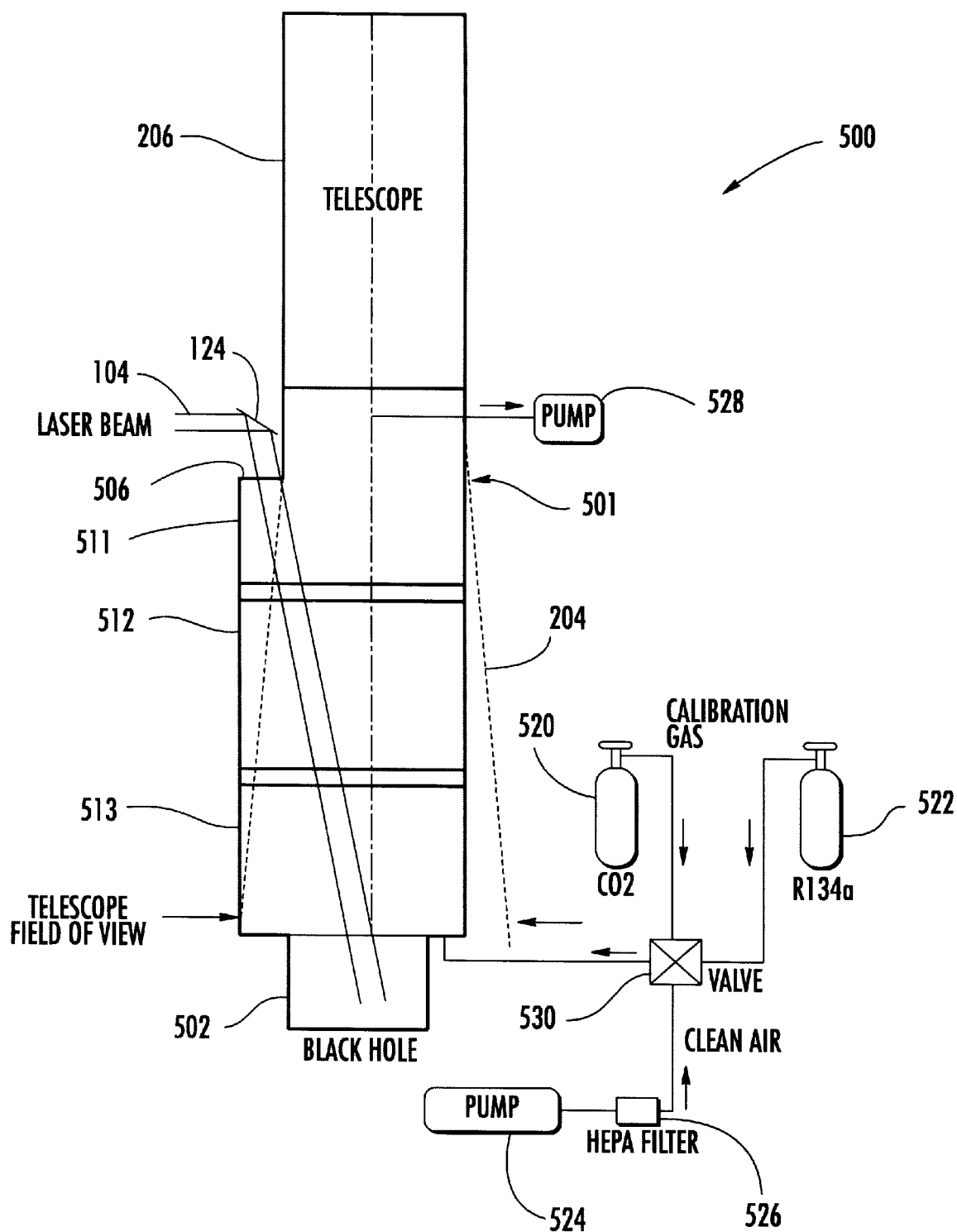
FIG. 6 is substantially a schematic view of a calibration tube used to calibrate the sensor of FIG. 1.

FIG. 6 shows a calibration tube used to calibrate system 20. Calibration tube 500 allows an absolute calibration of the backscattered signal. A tube 501 is directly attached to telescope 206 during calibration and has a beam terminus or black hole 502 at the opposite end. Tube 501 has three sections that are attached, sections 511, 512 and 513. Tube 501 is filled with a mixture of gases with a known backscatter coefficient. The gas is a mixture of CO2 gas 520, R134a gas 522 and clean air supplied by pump 524 through HEPA filter 526. A valve 530 mixes and meters the gases. A pump 528 assists in removing the calibration gas from tube 501. In this manner, the tube can be filled with a calibration gas with a well-known backscatter coefficient without using windows to enclose the tube. Windows would cause excessively large backscatter signals and thereby would effectively shorten the tube length available for calibration measurements. The laser beam 104 is introduced into tube 501 through a small window 506 on the side of the tube. However, window 506 is Dot in the field of view of the telescope and therefore does not cause a signal. By filling the tube with a calibration gas 504, for example $CO_2$, the backscattering coefficient is known and the backscattered signal can be calibrated in terms of an absolute backscatter coefficient. This procedure allows reproducibly to quantify the backscatter coefficient from aerosol particles such as those emitted or entrained by on-road vehicles.

Sensor 20 measures backscattering and/or transmission (also called extinction measurement) across the road before and after a vehicle passes. The difference between measurements before and after a vehicle passes are largely due to particles emitted by the vehicle and are used to derive columnar particle mass concentrations. The preferred embodiment uses a short-range lidar (light detection and ranging) system to measure range resolved particle backscattering across the road before and after a vehicle passes. The spatial and temporal distribution of these concentrations can be used to distinguish between entrained road dust and tail pipe particulate emissions. With the help of a carbon dioxide column concentration measured, for example, by a conventional RSD, the measurement of particle mass concentrations can be converted into a fuel based particulate mass emission rate.

The extinction measurement does not rely at all on the lidar principle, and the backscatter measurement can also be accomplished without the time resolution inherent in a lidar system. However, we use the lidar principle in the preferred embodiment to achieve range-resolved measurement of backscatter.

The use of ultraviolet light such as of a wavelength of 266 nm has several significant advantages compared to the infrared opacity method:

1. Solar background light does not have a detrimental influence on the measurement, as solar light below about 300 nm does not reach the earth's surface due to absorption in the heart's ozone layer. In other words, below 300 nm it is completely dark.

2. In the infrared part of the spectrum, light extinction due to particles in automotive tailpipe emissions is almost exclusively due to light absorption by elemental carbon (EC) and light scattering by both EC and OC (organic carbon) is extremely weak. EC and OC make up the vast majority of tailpipe particulate mass emissions for vehicles with combustion engines using carbon-based fuel. In the ultraviolet, both absorption by EC and scattering by both EC and OC contribute to extinction and backscatter signals. As the EC/OC mass ratio varies widely from vehicle to vehicle, ultraviolet measurements yield a measure of emitted particulate mass far superior to infrared or visible measurements.

3. In the ultraviolet, the scattering and extinction due to the small particles (typical mass mean diameter of 100 nm) emitted by automotive tailpipes is greatly enhanced compared to the infrared, while scattering and extinction due to the large road dust particles (typical mass mean diameter above 10,000 nm) is greatly reduced compared to the infrared. This results in a significant suppression of the signal due to entrained road dust in the ultraviolet, compared to operation at longer wavelengths such as in the infrared. This significant suppression is achieved even without the spatial and temporal discrimination against road dust (as possible with the lidar principle) and remains important if range-resolved detection of the backscatter signal is not utilized.

The particulate sensor system 20 can be used to measure additional particulate parameters such as emission rates, particles emitted per volume of fuel etc. For these measurements several additional pieces of information are needed. The $CO_2$ column content as a function of time to derive fuel based tail pipe emission rates, speed and acceleration of the vehicle, grade of the roadway, license plate and type of the vehicle. All these data are routinely acquired during conventional remote sensing device operation (RSD). Sensor 20 can be operated co-located with a conventional RSD or these functions can be integrated within sensor 20. For example, carbon dioxide detector 50 is shown as a part of sensor 20 in FIG. 1.

TABLE 1

| Component | Manufacturer | Model # |
| --- | --- | --- |
| Transmitter Subsystem | | |
| UV Laser | Nanolase | NU-10110-100 Head; NV-214-1 Controller |
| Beam Splitter | Thorlabs | |
| Photodiode Sensor | ThorLabs | Det210 |
| Adjustable Mirrors | New Focus | 9809 5108-A-UV |
| Spatial Filter | ThorLabs | KT310 + two lenses and a pin hole |
| Outgoing mirror | Newport | 1/2" UV-Enhanced Aluminum |

TABLE 1-continued

| Component | Manufacturer | Model # |
|---|---|---|
| Beam Terminus Receiver Subsystem | ThorLabs | 510 |
| Telescope | Custom | Tube, fused-silica lenses, mounting rings |
| Solar blind Filter | Corian | 5B-300-F |
| Spectral Filter | Corian | G10-265-F |
| Photomultiplier Tube Protection Circuit Subsystem | Hamamatsu | H6780-06 |
| Photosensors (Up- & Downstream) | Honeywell | PK86442 Head; PK86461 Base |
| Reflectors (Up- & Down-stream) | Honeywell | FE-RR8 |
| Laser Control Box Data Acquisition Subsystem | Custom-built | |
| Signal Splitter (Pick-off Tee) | Picosecond | 5520C |
| High-Speed Oscilloscope | Agilent (HP) | Infinium 54845A |
| Data Acquisition Computer Calibration Subsystem | Apple | PowerMac 8600 |
| Tube | Custom | |
| UV-Windows | Esco | Si-UV Quartz Disk 1" |
| Gas Delivery System | Custom | |
| Various Mounting Equipment | Several different manufacturers | |

Sensor System Operation

Particulate Sensor System 20 can perform two different types of particulate measurements. The two measurements are a transmission measurement (also called an opacity or extinction measurement) and a backscatter measurement (also called a range resolved measurement). The measurements of transmission and backscatter can be complementary. The transmission measurement is not very sensitive, but yields an accurate measurement even in very dirty (i.e., high optical density) exhaust plumes. The backscatter measurement is very sensitive but is likely to loose accuracy in very dirty exhaust plumes as the laser beam intensity is no longer constant across the plume. Use of both transmission and backscatter measurements can yield a sensor system with a high dynamic range and good accuracy over this range.

Backscatter Measurement

Referring back to FIGS. 1 and 5, the vehicle particulate sensor 20 is set up along a road or traffic lane, often on a highway onramp. The transmitter 100 and receiver 200 are placed on one side of the road and the beam terminus 140 and the two cat-eye reflectors 406, 408 for the protection system are located on the other side of the road. When a car passes by system 20 beam block signals are triggered by gates 401 and 402 and provided to laser control 302. A beam unblock signal follows in about 0.2–0.4 second, indicative of a passing car. Transmitter 100 then emits a short (<1 ns equivalent to <30 cm) laser pulse in a preferred wavelength of 266 nanometers which propagates across the road towards the beam terminus 140. The air between the transmitter and the beam terminus contains particles from the exhaust 45 of the vehicle. The air may also contain road dust or an ambient level of particles prior to the vehicle passing the transmitter. The particles in the air vary in density or concentration depending upon factors such as the wind and distance from the tailpipe 40. At various distances from the transmitter, some of the laser pulse 104 is backscattered by the ambient road dust and/or the vehicle-generated particles. The backscattered light 202 is received by the receiver 200. The photomultiplier tube 214 generates a backscattered signal S(r) that is supplied to the data system 300 to calculate particulate density and other particle parameters. The backscattered light 202 arrives at different times at the receiver 200 depending on its roundtrip distance from the transmitter to scattering location and back to the receiver. Arrival time is connected with the roundtrip distance by the speed of light, with a time of 1 ns corresponding to a roundtrip distance of about 15 cm. Using the timing signal indicating the start of a laser pulse and the arrival time at the receiver, the data system 300 can calculate a range location of the particles across the road. With the current component speeds of system 20, the system is able to register a spatially resolved backscatter signal with a spatial resolution of about 15 cm. In other words, the system is able to look for particles in 15 cm ranges across the road. Higher spatial resolutions can be realized if faster detectors, electronics, and lasers with shorter pulse length are used.

Measurements of particles are performed prior to the vehicle passing system 20 and after passing system 20. The measurement of particles prior to the vehicle passing determines an ambient level of particulate matter. The measurement of particles after the vehicle passes is a measurement of a combination of the ambient level of particulate matter, the road dust entrained by the vehicle, and the particles due the exhaust gas of the vehicle. Data system 300 collects data for both measurements, before and after passing system 20. A typical vehicle is from 1.5–1.8 m wide, with a sampling distance of 15 cm, this gives approximately 10–12 ranges or range gates across the back of the car from which particle measurements can be obtained. If the exhaust stream exits at the side of the car, more range gates of interest are possible. The system geometry is bi-axial. This results in more flexibility for tailoring sampling overlap function (compared to a co-axial system) and thereby reducing the dynamic range of the return signal. With an approximate pulse repetition rate of 6 kHz, backscatter from 3000 pulses, with 40–50 range gates each, are collected in the half-second following the passage of the car. The range resolved particle data that results from the backscattered measurement permits discrimination of road dust thrown up by the tires from particulate matter in the exhaust plume. For example, measurements for a typical car with a rear exhaust show larger amounts of particles in the spaced apart tire ranges and smaller amounts of particles between the tires. This is due to the fact that the tires are increasing the amount of road dust in the air.

Transmission Measurement

The backscatter signal from the beam terminus is used to measure optical transmission (i.e., opacity) through the overall length of the exhaust gas being tested. This is called a transmission measurement. This is useful as an alternative evaluation of total path-integrated particle mass, and to evaluate the lidar ratio (i.e., backscatter phase function) which depends on the particle size distribution. This can be used to assess the ratio of the fine particles emitted by the tail pipe and the coarse particles entrained from the road.

Transmitter 100 and receiver 200 are placed on one side of the road and the beam terminus 140 and the two cat-eye reflectors 406, 408 for the protection system are located on the other side of the road. Transmitter 100 emits a short (<1 ns equivalent to <30 cm) laser pulse in a preferred wavelength of 266 nanometers which propagates across the road towards the beam terminus 140. The air between the transmitter and the beam terminus contains particles from the exhaust 45 of the vehicle. The air may also contain road dust or an ambient level of particles prior to the vehicle passing the transmitter. The particles in the air vary in density or concentration depending upon factors such as the wind and distance from the tailpipe 40. As the laser travels through the air some of the laser light energy is blocked or scattered by the particles. When the light reaches the beam terminus 140 some of it is backscattered to receiver 200 indicating the end of each pulse after approximately 40–50 ns, depending on the distance from the transmitter to the beam terminus. The backscattered light 202 is received by the receiver 200. The photomultiplier tube 214 generates a backscattered signal $S_{BH}$ that is supplied to the data system 300 to calculate particulate density and other particle parameters. The transmission measurement is therefore a measurement of particles that reside in the total distance between the transmitter and the receiver.

Using light in the ultraviolet wavelengths makes the transmission measurement sensitive to both light scattering (organic carbon particles) and absorbing particles instead of just light absorbing particles (i.e., black carbon particles) as is the case in the previously used infrared measurements.

In contrast to conventional remote sensing devices (RSD), the present invention is especially applicable to the characterization of particulate emissions from diesel powered vehicles as particulate emissions from diesel engines are generally much larger than those from gasoline engines. In addition, the characterization of road dust entrainment by vehicles is also an important application of the invention. Besides measuring emissions from on-road vehicles, the invention can also be used to measure particulate mass emissions from off-road vehicles such as locomotives, aircraft, construction, mining and military equipment and vehicles, snowmobiles, watercraft, and all-terrain vehicles. While conventional RSDs are mostly used in areas that are not in attainment with ozone standards (importance of $NO_x$ and HC emissions), the invention will be of most use in areas that are not in attainment with particulate (e.g., PM2.5 and PM10) emission standards.

Data Analysis

Transmission Measurement Calculation

The sensor system transmission signal $S_{BH}$ from the beam terminus or Black Hole (BH) can be used to calculate the change in transmission or opacity due to the car exhaust. Alternatively, the beam terminus can be replaced by a UV mirror that reflects the laser beam back to the main instrument where its signal is measured by a detector. In this case, the signal $S_{BH}$ would stand for the signal measured by this detector after two-way transmission through the exhaust gas plume 45. Alternatively, this detector could be placed on the other side of the road, directly replacing the beam terminus and measuring the one-way transmission signal. In this case, the factor two (2) in the exponential of eq. 1.1 needs to be replaced by one (1). The following signals are used:

$S_{BH\_B}$ The BH background signal, i.e., the signal after two-way transmission through the atmosphere before the car passes by the sensor 20. This signal is used as reference and corresponds to a transmission $T\sim 1$.

$S_{BH\_CB}$ The BH signal measured behind the car with exhaust, entrained road dust etc. reducing the signal.

The car-induced reduction in two-way transmission between transmitter location $r_0$ and BH location $r_1$ can be expressed as transmission $T_C(r_0,r_1)$ with $$T_C(r_0, r_1) = \frac{S_{BH\_CB}}{S_{BH\_B}} = \exp\left[-2\int_{r_0}^{r_1} \sigma_C(r)dr\right], \quad (1.1)$$

where $\sigma_C$ is the car-induced extinction coefficient (unit: $m^{-1}$). To determine the BH signals $S_{BH}$ from the range resolved BH signals $S_{BH}(r)$, the range resolved signal needs to be integrated over r. This can be done by fitting a Gaussian function to $S_{BH}(r)$ and using its area or by another numerical integration technique.

Fuel Based Particulate Mass Emission Rate Calculation Using the Transmission Measurement A fuel based particulate mass (PM) emission rate can be derived only for PM emitted by the tail pipe using the simultaneously emitted $CO_2$ as a tracer. No such tracer (to determine plume dilution) exists for entrained road dust. In addition, the transmission method is incapable of distinguishing between tail pipe emission and entrained road dust. Therefore, in this example, we use the assumption that the influence of entrained road dust on the measured transmission can be neglected. The validity of this assumption depends on the specific situation and can be checked using backscattered or range-resolve measurements. For suspended particles with a mass concentration $C_{PM}$ (unit: $g/m^3$) we define a mass-based extinction efficiency $\sigma_{eff}$ (unit: $m^2/g$) as $$\sigma_{eff} = \frac{\sigma}{C_{PM}}. \quad (1.2)$$

For homogeneous spherical particles with a known size distribution, complex refractive index, and density, $\sigma_{eff}$ can be calculated using Mie theory. Another approach is to evaluate $\sigma_{eff}$ empirically for tail pipe emissions with in situ instrumentation. Once $\sigma_{eff}$ is known for tail pipe emission (let's call it $\sigma_{eff\_TP}$) equation 1.1 can be written, with the help of equation 1.2, for particle mass concentrations $$T_C(r_0, r_1) = \exp\left[-2\sigma_{eff\_TP}\int_{r_0}^{r_1} C_{PM\_TP}(r)dr\right]. \quad (1.3)$$

The integrated (i.e., column content) mass concentration $IC_{PM\_TP}$ (unit: $g/m^2$) can be written as $$IC_{PM\_TP}(r) = \int_{r_0}^{r_1} C_{PM\_TP}(r)dr = \frac{-\ln[T_C(r_0, r_1)]}{2\sigma_{eff\_TP}} \quad (1.4)$$

At the same time, the carbon dioxide detector 50 or a conventional RSD measures the integrated (i.e., column content) mass concentration of tail pipe $CO_2$ (i.e., above ambient) labeled $IC_{CO2\_TP}$ (unit: $g/m^2$) yielding the PM-$CO_2$ mass ratio PM/$m_{CO2}$ (unit: g-PM/g-$CO_2$) as $$\frac{PM}{m_{CO2}} = \frac{IC_{PM\_TP}(r)}{IC_{CO2\_TP}} = \frac{-\ln[T_C(r_0, r_1)]}{2\sigma_{eff\_TP}IC_{CO2\_TP}} \quad (1.5)$$

The fuel carbon content cc (unit: g/liter) can be expressed in terms of carbon mass $m_C$ and fuel volume $V_{fuel}$ $$cc = \frac{m_C}{V_{fuel}}. \quad (1.6)$$

Under the assumption that all fuel carbon is combusted into tail pipe $CO_2$ (this can be refined using RSD measured HC and CO integrated concentrations), the relationship between tail pipe emitted $CO_2$ mass $m_{CO2}$ and fuel carbon mass $m_C$ is $$\frac{m_{CO2}}{m_C} = \frac{(12 + 2 \times 16)}{12} = \frac{44}{12} = \frac{11}{3} = 3.6. \qquad (1.7)$$

Using equ. 1.6, equ. 1.5 can be rewritten to yield the PM tail pipe emission per liter of fuel consumed $PM/V_{fuel}$ as $$\frac{PM}{V_{fuel}} = cc\left(\frac{m_{CO2}}{m_C}\right)\frac{IC_{PM\_TP}(r)}{IC_{CO2\_TP}} = cc\left(\frac{m_{CO2}}{m_C}\right)\frac{-\ln[T_C(r_0, r_1)]}{2\sigma_{eff\_TP}IC_{CO2\_TP}} \qquad (1.8)$$

with $m_{CO2}/m_C$ defined by equ. 1.7.

Backscatter Measurement Calculation

The sensor signal S(r) can be written as function of distance (lidar equation)

$$S(r) = k\frac{O(r)}{r^2}\beta(r)T(r_0, r), \qquad (2.1)$$

where k is a constant, O is the overlap function, β is the backscatter coefficient (unit: $m^{-1}/sr$) and $T(r_0,r)$ is the two-way transmission between $r_0$ and r.

Specific LORAX signals of interest are $S_B$ The background signal, i.e., the signal from the homogeneous atmosphere before the car passes by the sensor.

$S_{CB}$ The signal measured behind the car with exhaust, entrained road dust etc. added to the background signal $S_B$.

$S_C = S_{CB} - S_B$ The signal added by the car (exhaust, entrained dust, etc.) to the ambient signal.

This assumes that scattering particles are added to the ambient air. For example, a hypothetical Experimental Ultra-Low Emissions Vehicle (XULEV) emitting HEPA-filtered air through its tail pipe would result in a negative $S_C$ as it would effectively emit aerosol with fewer particles than the ambient air. $S_C$ is therefore a measure of the difference in signal between after the car passes and before it passes. This problem occurs because the ambient concentration of our dilution tracer ($CO_2$) passes largely unmodified though the combustion-exhaust system while this cannot be assumed for ambient PM concentrations. However, ambient PM concentrations are expected to be much smaller than tail pipe PM concentrations. The analysis can be significantly simplified if $T(r_0,r)=1$ is assumed. In most cases, this is true within 10%. This assumption can be checked by measuring the transmission from the BlackHole reflection (see transmission analysis section 1). For $T(r_0,r)=1$ the LORAX signal can be written as $$S(r) = k\frac{O(r)}{r^2}\beta(r), \qquad (2.2)$$

and $$S_C(r) = S_{CB}(r) - S_B(r) = k\frac{O(r)}{r^2}[\beta_{CB}(r) - \beta_B(r)] = k\frac{O(r)}{r^2}\beta_C(r), \qquad (2.3)$$

with $\beta_C$ defined as $\beta_C = \beta_{CB} - \beta_B$. In addition, $S_{cal}$, the signal from a calibration gas, enclosed in a tube, with known backscatter coefficient $\beta_{Cal}$ is measured as $$S_{Cal}(r) = k\frac{O(r)}{r^2}\beta_{Cal}(r). \qquad (2.4)$$

The backscatter coefficient $\beta_C$ due to the car can be determined as $$\beta_C(r) = \beta_{Cal}(r)\frac{S_C(r)}{S_{Cal}(r)} \qquad (2.5)$$

Fuel Based Particulate Mass Emission Rate Calculation Using the Backscatter Measurement A fuel based PM emission rate can be derived only for PM emitted by the tail pipe using the simultaneously emitted $CO_2$ as a tracer. No such tracer (to determine plume dilution) exists for entrained road dust. The determination of road dust entrainment rates relys on assumptions, knowledge, or measurements of the dispersion process tailored to the specific situation and is not discussed here. The part of $\beta_C$ due to tail pipe emission called $\beta_{C\_TP}$ can be determined by modeling the spatial distribution of the tail pipe PM emissions and the entrained PM and fitting the sum of these distributions to $\beta_C$ as measured by LORAX. For suspended particles with a mass concentration $C_{PM}$ (unit: $g/m^3$) we define a mass-based backscattering efficiency $\beta_{eff}$ (unit: $m^2/g/sr$) as $$\beta_{eff} = \frac{\beta}{C_{PM}}. \qquad (2.6)$$

For homogeneous spherical particles with a known size distribution, complex refractive index, and density, $\beta_{eff}$ can be calculated using Mie theory. Another approach is to evaluate $\beta_{eff}$ empirically for tail pipe emissions. Once $\beta_{eff}$ is known for tail pipe emission (let's call it $\beta_{eff\_TP}$) equation 2.5 can be written, with the help of equation 2.6, for particle mass concentrations $$C_{PM\_TP}(r) = \frac{\beta_{Cal}(r)}{\beta_{eff\_TP}}\frac{S_{C\_TP}(r)}{S_{Cal}(r)}. \qquad (2.7)$$

The next step involves integrating the mass concentration $C_{PM\_TP}$ over the same distance as the path integrated $CO_2$ measurement, say from $r_0$ to $r_1$ yielding the integrated (i.e., column content) mass concentration $IC_{PM\_TP}$ (unit: $g/m^2$)

$$IC_{PM\_TP}(r) = \frac{1}{\beta_{eff\_TP}}\int_{r_0}^{r_1}\beta_{Cal}(r)\frac{S_{C\_TP}(r)}{S_{Cal}(r)}dr \qquad (2.8)$$

At the same time, the conventional RSD measures the integrated (i.e., column content) mass concentration of tail pipe $CO_2$ (i.e., above ambient) labeled $IC_{CO2\_TP}$ (unit: $g/m^2$) yielding the PM-$CO_2$ mass ratio $PM/m_{CO2}$ (unit: g-PM/g-$CO_2$) as $$\frac{PM}{m_{CO2}} = \frac{IC_{PM\_TP}}{IC_{CO2\_TP}} = \frac{1}{IC_{CO2\_TP}\beta_{eff\_TP}}\int_{r_0}^{r_1}\beta_{Cal}(r)\frac{S_{C\_TP}(r)}{S_{Cal}(r)}dr \qquad (2.9)$$

Using equ. 1.6, equ. 2.9 can be rewritten to yield the PM tail pipe emission per liter of fuel consumed $PM/V_{fuel}$ as $$\frac{PM}{V_{fuel}} = \quad (2.12)$$

$$cc\left(\frac{m_{CO2}}{m_C}\right)\frac{IC_{PM\_TP}(r)}{IC_{CO2\_TP}} = \frac{cc\left(\frac{m_{CO2}}{m_C}\right)}{IC_{CO2\_TP}\beta_{eff\_TP}}\int_{r_0}^{r_1}\beta_{Cal}(r)\frac{S_{C\_TP}(r)}{S_{Cal}(r)}dr$$

with $m_{CO2}/m_C$ defined by equ. 1.7.

If the lidar principle is not utilized, the measurement of backscatter is in itself range-integrated; the analysis does not use range-resolved variables and the integration introduced in eq. 2.8 is not necessary to derive the PM column content.

An advantage of vehicle particulate sensor system is that it is capable of measuring particle emissions from vehicles passing the sensor in dense traffic. The sensor yields spatial resolution across the road combined with high time resolution. Another advantage of the sensor is that is can distinguish between tail pipe particle emissions and entrained road dust. Another advantage of the present invention is that it operates at an ultraviolet wavelength which results in strong scattering from the small particles (typically sub-micron size) contained in tail pipe emissions. Another advantage of the particulate sensor is that it operates in the solar-blind spectral region (i.e., below about 300 nm), where the invention detects the scattered light with very high sensitivity due to the absence of background light. Another advantage of the present invention is that it can measure both organic carbon and black carbon particles.

CONCLUSION

The present invention solves many of the problems associated with the prior art. The present invention provides a vehicle particulate sensor system that can discriminate between ambient road dust and particulate exhaust due to a vehicle. The present invention further provides a vehicle particulate sensor that call detect both organic carbon and black carbon particles. The present invention provides a vehicle particulate sensor that can quickly and easily be deployed by at a roadside location to measure the particulate emissions from multiple vehicles as they pass a test site.

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

What is claimed is:

1. An apparatus for measuring particles in a gas, comprising:
   (A) a transmitter adapted to provide a source of ultraviolet radiation, the source of radiation being a laser, the radiation traveling through the gas and impinging on the particles in the gas generating a backscattered radiation, the radiation being terminated by a beam terminus, the transmitter generating a timing signal;
   (B) a receiver located in proximity of the transmitter, the receiver adapted to receive the backscattered radiation and to generate a backscattered signal indicative of the quantity of particles entrained in the gas; and
   (C) a data system connected to the receiver, the data system adapted to receive the timing signal and the backscattered signal as an input and to calculate a quantity of particles in the gas at a location from the transmitter.

2. The apparatus according to claim 1, wherein a beam splitter is located in the path of the radiation, the beam splitter adapted to split off a portion of the radiation and to direct the portion of the radiation onto a photodiode, the photodiode generating the timing signal.

3. The apparatus according to claim 1, wherein a beam steering optic assembly is located between the beam terminus and the transmitter, the beam steering optics adapted to direct and align the radiation.

4. The apparatus according to claim 3, wherein a spatial filter is located between the beam terminus and the beam steering optics.

5. The apparatus according to claim 1, wherein the receiver further comprises:
   (A) a telescope to collect the backscattered radiation;
   (B) an aperture mounted adjacent the telescope to adjust the field of view of the telescope;
   (C) a filter mounted adjacent the aperture to remove unwanted wavelengths of the backscattered radiation; and
   (D) a photomultiplier tube mounted adjacent the filter, the photomultiplier tube receiving the backscattered radiation and generating the backscattered signal.

6. The apparatus according to claim 1, wherein the data system further comprises:
   (A) an analog to digital converter adapted to convert the backscattered signal and the timing signal to digital signals;
   (B) a processor connected to the analog to digital converter, the processor adapted to perform calculations on the digital signals.

7. The apparatus according to claim 1, further comprising: a protection system, the protection system comprising:
   (A) a pair of optical gates mounted on each side of the transmitter; and
   (B) a pair of reflectors mounted on each side of the beam terminus, the optical gates forming an optical path between the reflector and the optical gate, the optical gate turning off the transmitter when the optical path is blocked.

8. The apparatus according to claim 1, wherein the apparatus is mounted adjacent a road with the radiation traveling across the road, the apparatus adapted to measure the particles in an exhaust gas of a vehicle passing on the road.

9. The apparatus according to claim 8, wherein a first measurement of particles is performed prior to the vehicle passing the apparatus and a second measurement of particles is performed after the vehicle passes the apparatus, the first measurement indicative of an ambient density of road dust, the second measurement indicative of the density of particles in the exhaust gas and the density of the road dust.

10. The apparatus according to claim 9, wherein the second measurement is subtracted from the first measurement to obtain the density of exhaust particles.

11. The apparatus according to claim 10, further comprising a carbon dioxide detector, the carbon dioxide detector measuring the concentration of carbon dioxide in the exhaust gas of the vehicle.

12. The apparatus according to claim 11, wherein the concentration of carbon dioxide is used to calculate a ratio of the density of exhaust particles to a volume of fuel consumed by the vehicle.

13. A system for measuring particles from an exhaust gas of a vehicle, the system comprising:
   (A) a laser adapted to provide a source of ultraviolet light, the light passing through the gas, the light impinging upon particles in the gas and generating a backscattered light;

(B) a beam terminus adapted to terminate the light, the beam terminus located along a linear path traveled by the light;

(C) a receiver located adjacent the laser, the receiver adapted to receive the backscattered light and to provide a backscattered light signal that is proportional to the number and size of the particles; and (D) a data system communicated with the receiver, the data system adapted to receive the backscattered light signal as an input and to provide at least one particle parameter as an output.

14. The system according to claim 13, wherein the laser provides a pulsed source of light, the data system operable to determine an elapsed time between transmitting a pulse of light and receiving the backscattered light and to determine the quantity of particles at a plurality of distances from the laser.

15. The system according to claim 14, wherein the system is adapted to discriminate between the particles at a tire location and the particles at an exhaust pipe location.

16. The system according to claim 14, wherein a first measurement of particles is performed prior to a vehicle passing the laser to obtain an ambient level of road dust and a second measurement of particles is performed after the vehicle passes the laser, the second measurement indicative of a combination of the ambient level of road dust and the particles in the exhaust gas.

17. The system according to claim 16, wherein the second measurement is subtracted from the first measurement in order to obtain the particles in the exhaust gas.

18. The system according to claim 13, wherein a laser control system is connected to the laser, the laser control system operable to control the laser.

19. The system according to claim 13, further comprising a carbon dioxide detector, the carbon dioxide detector adapted to measure a carbon dioxide concentration and to provide a carbon dioxide signal to the data system.

20. The system according to claim 13, further comprising a calibration tube that is attachable to the receiver, the calibration tube adapted to provide a known backscattered light signal to the receiver in order to calibrate the system.

21. The system according to claim 13, wherein the light has a wavelength less than 300 nanometers such that the effects of visible light on the receiver are eliminated.

22. The system according to claim 13, wherein the system is adapted to detect both organic carbon particles and black carbon particles.

23. A method of measuring particle density in an exhaust gas of a vehicle comprising:

A) measuring an ambient particle density prior to the vehicle passing a measurement location;

B) allowing the vehicle to pass the measurement location;

C) measuring a first particle density after the vehicle passes; and

D) calculating the particle density of the exhaust gas by subtracting the ambient particle density from the first particle density.

24. The method of measuring particle density according to claim 23, further comprising:

(A) measuring a carbon dioxide level at the measurement location;

(B) calculating a volume of fuel associated with the carbon dioxide level; and (C) calculating a ratio of particle density per volume of fuel.

25. A method of measuring particles from an exhaust gas of a vehicle comprising:

(A) transmitting an ultraviolet light across a vehicle path, the ultraviolet light impinging upon the particles generating a backscattered light;

(B) generating a timing signal;

(C) terminating the ultraviolet light;

(D) receiving the backscattered light;

(E) generating a backscattered signal proportional to the backscattered light; and (F) calculating a density of particles from the exhaust gas using the timing signal and the backscattered signal.

26. The method according to claim 25, further comprising: calculating the density of particles at a plurality of locations in the vehicle path.

27. The method according to claim 25, further comprising:

(A) transmitting the ultraviolet light across the vehicle path prior to the vehicle passing;

(B) calculating an ambient particle density;

(C) transmitting the ultraviolet light across the vehicle path after the vehicle passes;

(D) calculating a first density of particles, the first density of particles being a combination of the ambient particle density and the particle density of the exhaust gas; and (E) calculating the density of particles of the exhaust gas, the density of particles of the exhaust gas being the difference between the first density of particles and the ambient particle density.

28. The method according to claim 27, further comprising:

(A) measuring a carbon dioxide level;

(B) calculating a volume of fuel associated with the carbon dioxide level; and (C) calculating a ratio of the density of particles in the exhaust gas per the volume of fuel.

29. A system for measuring particles from an exhaust gas of a vehicle, the system comprising:

(A) a laser adapted to provide a source of ultraviolet light, the light passing through the gas, the light impinging upon particles in the gas reducing the intensity of the light;

(B) a beam terminus adapted to terminate the light, the beam terminus located along a linear path traveled by the light, the beam terminus generating a reflected light;

(C) a receiver located adjacent the laser, the receiver adapted to receive the reflected light and to provide an electrical signal that is proportional to the number and size of the particles; and (D) a data system communicated with the receiver, the data system adapted to receive the backscattered light signal as an input and to calculate a density of particles.

30. The system for measuring particles according to claim 29, wherein the particles are organic carbon and black carbon particles.

* * * * *